United States Patent [19]

Lobello

[11] Patent Number: 5,106,380
[45] Date of Patent: Apr. 21, 1992

[54] SYRINGES

[76] Inventor: Diane Lobello, 6100 Laurent Dr., Parma, Ohio 44129

[21] Appl. No.: 648,917

[22] Filed: Feb. 1, 1991

[51] Int. Cl.⁵ .............................................. A61M 5/32
[52] U.S. Cl. .................................... 604/198; 604/263
[58] Field of Search ................ 604/198, 187, 192, 263

[56] References Cited

U.S. PATENT DOCUMENTS

| | | | |
|---|---|---|---|
| 4,927,018 | 5/1990 | Yang et al. | 604/263 X |
| 4,927,417 | 5/1990 | Moncada et al. | 604/198 |
| 4,976,702 | 12/1990 | Andrews et al. | 604/198 |
| 4,998,920 | 3/1991 | Johnson | 604/263 X |

Primary Examiner—John D. Yasko
Attorney, Agent, or Firm—J. Helen Slough

[57] ABSTRACT

A tubular guard is provided by this invention which can be telescoped over the barrel of a syringe or other device carrying a needle adapted for injection or removal of fluid of a patient or animal and which can be locked into barrel covering position thereover, means whereby locking engagement of the guard and the barrel may be broken, guide means for guiding the guard into telescoped needle or nozzle surrounding position after use of the syringe, said guard being adapted to be maintained into the nozzle or needle surrounding position and means whereby the guard is preventing from returning to its initial barrel covered position.

2 Claims, 2 Drawing Sheets

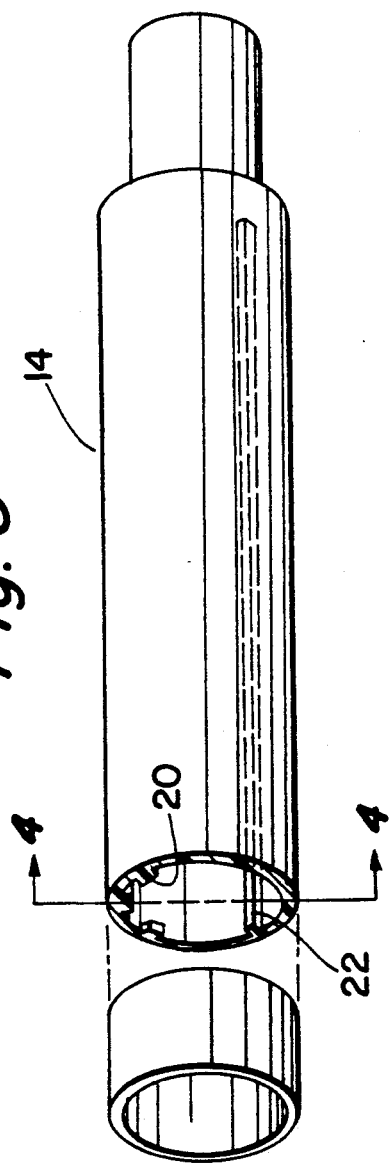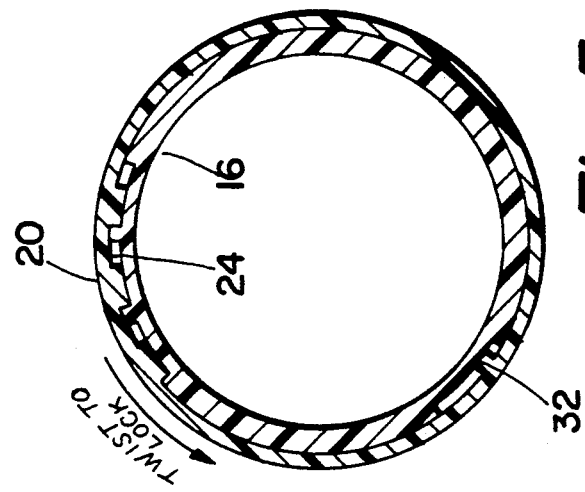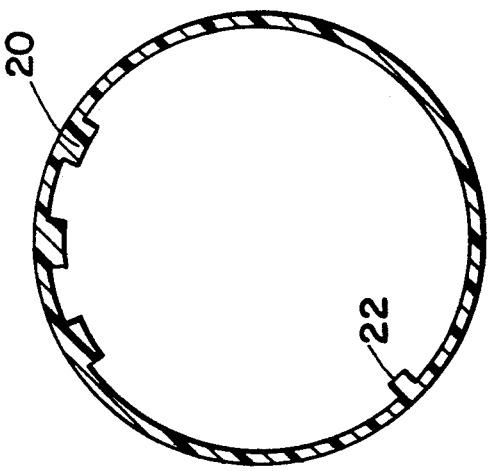

SYRINGES

FIELD OF THE INVENTION

This invention relates to a syringe and guard therefore and relates more particularly to a syringe having a guard for prevention of accidental puncturing of an individual by the needle of the syringe.

BACKGROUND OF THE INVENTION

In the past, problems have existed in the disposal of medical waste. At present, syringes are generally capped. With the advent of the "Aids" epidemic, accidental pricking of the needle of the syringe has been found to result in death. Care in the disposition of medical waste is hence essential. The present invention presents a solution to the problems of the past in that once a syringe has been used the user need only move an adjustable guard provided thereon, which guard is an integral part of the syringe, from a fixed position covering the barrel of the syringe and draw the same over that portion of the syringe containing the needle to cover the needle of the syringe and lock the same in position thereover. The guard when so locked ensures complete coverage of the needle for throw away and the guard in such adjusted position completely covers the needle preventing the needle from in any manner coming into contact with anyone carrying or disposing of the same.

An object of this invention is to produce a syringe which can be used and disposed of safely. A further object of the invention is to produce a guard integrally associated with the syringe which is adapted to be drawn from its initial mounting on the syringe wherein the needle of the syringe is exposed for its intended use and the guard, after injection, of the needle is adjustably moved to needle covering position wherefor that the syringe can be safely disposed of. A further object of this invention is to construct a guard for a syringe which is inexpensive to manufacture, highly efficient in use and safe in handling.

SUMMARY OF THE INVENTION

The present invention involves an improvement in a syringe, which improvement involves the provision of a guard which is an integral part of the syringe. The guard is preferably formed with a cylindrically-shaped body which encircles the barrel of the syringe. The guard is preferably formed of transparent plastic. The said improved syringe is adapted for use in the manner of a regular syringe throughout the injection of medication thereby. After use of the syringe the individual who administers the injection to a patient or other person is able to move the guard from its initially fixed position on the syringe which does not interfere with the use of the needle and is able to draw the guard over the needle where it is locked into a final non-reversible needle surrounding position wherefor anyone handling or otherwise contacting the used syringe is protected from any contact with the needle of the same. The improvement of the invention can be applied to devices used for the injection or removal of fluid by means of a needle into or from the body of a patient or animal receiving the same.

DESCRIPTION OF THE DRAWINGS

FIG. 3 is an exploded perspective view of the guard with an end guard;

FIG. 4 is a cross-sectional view taken from the line 4—4 of FIG. 3 showing molded teeth provided on the interior of the guard; and FIG. 5 is a cross-sectional view showing the teeth projecting inwardly of the guard.

DESCRIPTION OF THE PREFERRED EMBODIMENT

Figure 1:
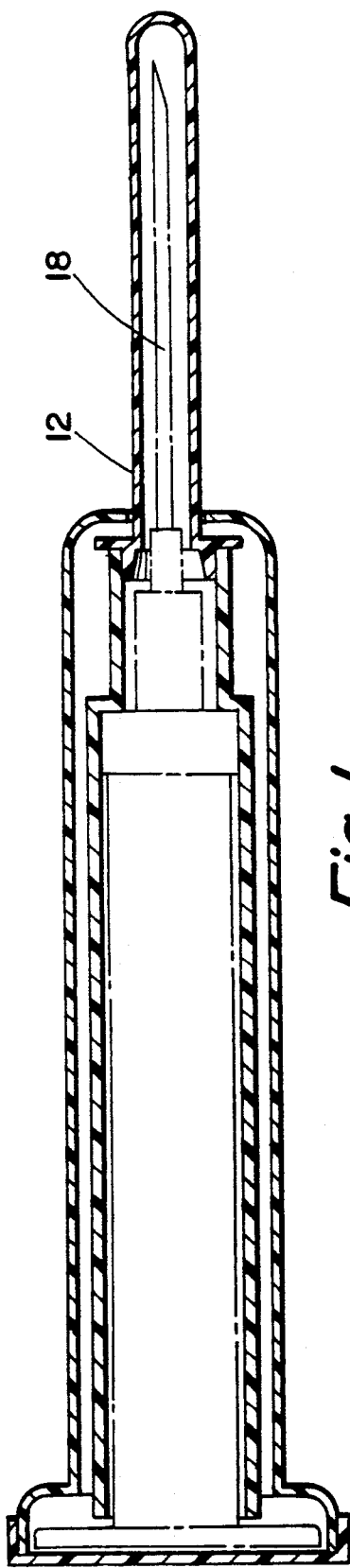
FIG. 1 is a cross-sectional view of the improved syringe and the guard of the invention shown plastic welded in a storage position within a shipping carton.
Figure 2:
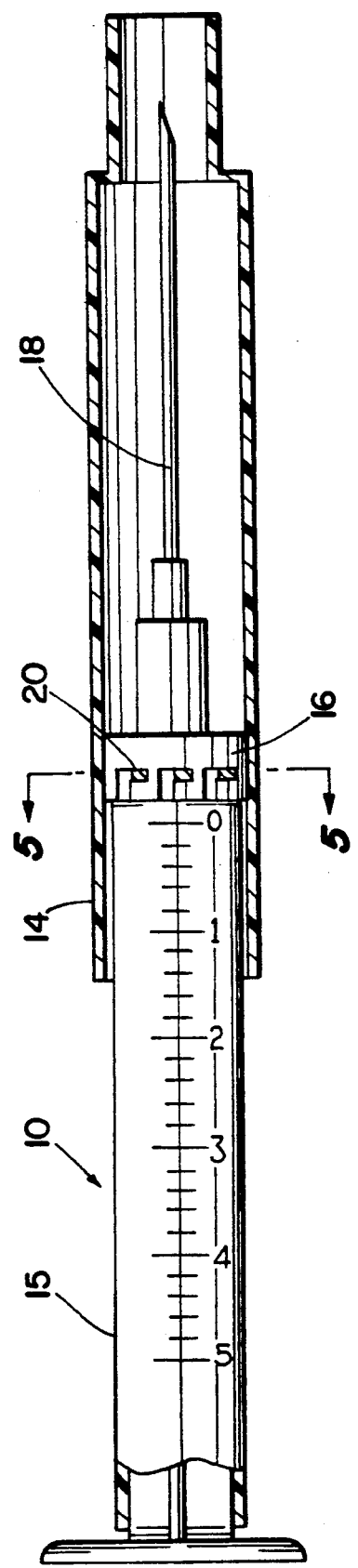
FIG. 2 is a cross-sectional view of the syringe and guard of FIG. 1 and discloses the safety guard deployed in needle protective position.

The present invention relates to a preferred embodiment of my invention, in all of which like parts are designated by like reference characters. In FIG. 1, I show a syringe of the prior art having a plastic cover thereon which may be removed for use of the syringe. In FIG. 2 at 10, I show the syringe of my invention with a guard 14, the locking guard 14 being an integral part of the syringe. FIG. 2 shows the cylindrical barrel 11 of the syringe completely covered by the guard 14 before and during use. Before use, the nozzle end or needle 18 of the syringe is covered by a protective cap 12 which is removed before insertion of medication into the syringe but which can be replaced if it is necessary after transporting the medication filled syringe to the patient. After injection of the patient, the guard 14 is drawn over the needle or nozzle 18 of the syringe. As shown in FIG. 2, the guard completely covers the needle 18, a portion of the guard extending beyond the outer end of the needle thus ensuring safety for anyone coming into contact with the syringe and avoids pricking of said person by the needle 18. FIG. 3 discloses the guard 14, which in a preferred embodiment, is constructed of clear plastic or other transparent material to enable a physician, nurse or other individual using the syringe to observe the contents of the syringe.

The guard 14 preferably has an open ended cylindrically shaped body which is adapted to be telescoped over the barrel 15 of the syringe. On the upper portion on the inside of the cylindrical tubular body of the guard 14 inwardly projecting lugs or teeth 20 are provided. The teeth 20 are, as shown, preferably adapted to be inserted into indentations 24 in a ring 16 encircling the lower portion of the syringe and are tapered. As shown in FIG. 4, a ring 16 is secured to the syringe downwardly of the needle end of the syringe. A guide 22 as shown in FIG. 3 are aligning the teeth into the ring and for affording projection of the guard over the needle portion of the syringe is shown disposed on the inside of the guard 14. The guide 22 comprises an elongated ridge internally of the guard extending from the site of the teeth 20 substantially the whole length of the barrel 10. A projection 32 in the ring 16 is adapted to ride in the internal guide 22 for projection of the guard forwardly from the barrel to the needle end of the syringe. FIG. 5 shows the guard, as seen from the top end of the barrel, looking downward. Lugs or teeth 20 on the guard 14 extend about the inner circumference thereof and are tapered wherefor when the guard is moved on the guide to needle surrounded position, movement of the guard downwardly and away from the needle is prevented by the lugs or teeth as these are tapered outwardly as shown in FIG. 2.

In operation, the modified syringe with guard operates in a similar manner to a regular syringe up to a point after an injection. Basically the person using the syringe for injection first removes the syringe from the shipping carton twisting the plastic welds "W" and removing the cover therefrom and removing the protective cap 12 of the syringe. Medication is then drawn into the syringe and the area on the patient for the intended injection cleansed, after which the patient is given the injection. At said time the guard 14 is locked on the barrel of the syringe. After injection is given the individual giving the injection twists the guard 14 to break the weld of the guard 14 to the barrel of the syringe and then further twists the guard until the internal guide 22 matches up with a lug or tooth 32 in the ring 16 of the syringe. The guard then is able to be slidably moved into deployment for disposal of the syringe by any individual using the same and the guard is drawn over the needle securely locked in place. The syringe is now ready for disposal, the guard 14 surrounding and extending beyond the full length of the needle thus preventing any individual handling the same to become pricked by the needle.

The guard 14 is simple in manufacture. As stated above, it may be molded of clear plastic so that the unit of measure on the syringe can be read by the user. The teeth 20 are preferably tapered to have the edges thereof of greater width than the roots thereof for the purpose of preventing any return movement of the guard once the same is placed in needle surrounding position. The internal guide 22 may be molded into the clear plastic guard. The ring 16 around the syringe may also be molded by the same process by which the syringe is molded or can be molded separately and welded or glued to the syringe. After the ring 16 is in place the guard is placed on the syringe in the position, as shown in FIG. 1, and the guard spot-welded to the syringe. The welds are susceptible to being broken when the guard is twisted so that, in operation, the welds are broken when twisted and the guard extended after the injection had been given.

The present invention relates to a syringe provided with a locking guard which is an integral part of the syringe. FIG. 1 shows the modified syringe and guard in a storage position in a shipping container. As can be seen from the figure, the barrel of the syringe is completely covered by the guard in the storage container. The barrel 10 of the syringe remains completely covered by the guard 14 before and during use. Before use, the needle 18 is covered with the protective cap 12. Once the syringe has been used the guard 14 is drawn out to a locked position as shown in FIG. 2 in which it surrounds the needle 18 thus making the syringe safe for further handling or disposal.

The term "syringe" as used herein covers ampoules and other medical devices supplying a needle for injection or removal of fluid material from a patient or animal.

The invention has been described in connection with a preferred embodiment and it is to be understood that numerous and extensive departures and modifications may be made without however department from the scope of the invention which is intended to be limited only by the scope of the appended claims.

What is claimed is:

1. A syringe comprising a cylindrical barrel and a nozzle or needle comprising:
   a. a guard mounted on the barrel of the syringe;
   b. means locking the guard on the said barrel;
   c. means whereby the guard may be unlocked from its barrel mounted position and slidably moved into telescoped position over the nozzle or needle end of the syringe and locked into non-reversible needle surrounding position thereover;
   d. the guard comprises:
      1. a transparent cylindrical body adapted to fit over the barrel of the syringe;
      2. a ring encircling and secured to the lower portion of the syringe having indentations therein;
      3. means mounted on the cylindrical body of the guard having inwardly projecting lugs adapted to interlock with the indentations in the ring and to maintain the same in nozzle or needle covering position;
      4. a guide having an elongated ridge internally of the guard; and
      5. a projection in the ring riding in the guide adapted to project the guard forwardly from the barrel end of the syringe upon the exertion of manual twisting of the guard matching the guide with a lug on the ring drawing the body of the guard over the needle and locking the same thereover.

2. A syringe as in claim 1 wherein locking means are adapted to irreversibly lock the guard into the nozzle or needle covering position.

* * * * *